United States Patent [19]

Buchegger et al.

[11] Patent Number: 5,047,507

[45] Date of Patent: Sep. 10, 1991

[54] MONOCLONAL ANTIBODIES WITH SPECIFICITY AND HIGH AFFINITY FOR HUMAN CARCINOEMBRYONIC ANTIGEN

[75] Inventors: Franz Buchegger, Chexbres; Jean-Pierre Mach, Lausanne, both of Switzerland

[73] Assignee: Research Corporation Technologies, Inc., Tucson, Ariz.

[21] Appl. No.: 293,467

[22] Filed: Jan. 4, 1989

[30] Foreign Application Priority Data

Jan. 5, 1988 [GB] United Kingdom ............... 8800078

[51] Int. Cl.$^5$ .............. C07K 15/28; C12P 21/08; C12N 5/20; A61K 43/00
[52] U.S. Cl. ................. 530/387; 530/388; 530/389; 435/70.21; 435/172.2; 435/240.27; 424/1.1; 935/104; 935/107; 935/108; 935/110
[58] Field of Search ............. 424/1.1, 85.8, 88; 530/387-389; 435/7, 70.21, 172.2, 240.27, 7.9, 7.91, 7.92; 935/100, 104, 107, 110

[56] References Cited

U.S. PATENT DOCUMENTS

4,361,544 11/1982 Goldenberg ................. 424/1

FOREIGN PATENT DOCUMENTS

0098162 1/1984 European Pat. Off.

OTHER PUBLICATIONS

Hedin, A., et al., *International Journal of Cancer,* 30:547-552, (1982).

Haskell, C. M., et al., *Cancer Research,* 43:3857-3864, (Aug. 1983).
Hedin, A., et al., *Molecular Immunology,* 23:1053-1061, (1986).
Buchegger, F., et al., *International Journal of Cancer,* 41:127-134, (1988).
Accolla et al., Proc. Natl. Acad. Sci. U.S.A., vol. 77, No. 1, pp. 563-566, Jan., 1980.
Mach et al., Immunology Today, 2, pp. 239-249, Dec., 1981.
Buchegger, et al., Immunology Letters, 5, 1982, pp. 85-91.
Buchegger, et al., J. Exp. Med., 158, pp. 413-427 (1983).
Buchegger, et al., Int. J. Cancer, 33, pp. 643-649 (1984).
Paxton, et al., Proc. Natl. Acad. Sci. U.S.A., vol. 84, pp. 920-924, Feb., 1987.

*Primary Examiner*—Margaret Moskowitz
*Assistant Examiner*—Robert D. Budens
*Attorney, Agent, or Firm*—Wenderoth, Lind & Ponack

[57] ABSTRACT

The invention concerns novel monoclonal antibodies with high specificity to and affinity for human carcinoembryonic antigen (CEA), derivatives thereof, processes for the preparation of these antibodies and their derivatives, hybridoma cell lines secreting the antibodies, and processes for the preparation of said cell lines. The monoclonal antibodies of the invention and their derivatives are useful in the diagnosis and therapy of cancer and serial monitoring of cancer patients for recurrent disease or response to therapy. Test kits and pharmaceutical compositions containing said monoclonal anti-CEA antibodies are also subject of the invention.

9 Claims, No Drawings

MONOCLONAL ANTIBODIES WITH SPECIFICITY AND HIGH AFFINITY FOR HUMAN CARCINOEMBRYONIC ANTIGEN

The invention concerns novel monoclonal antibodies with high specificity to and affinity for human carcinoembryonic antigen (CEA), derivatives thereof, processes for the preparation of these antibodies and their derivatives, hybridoma cell lines secreting the antibodies, processes for the preparation of said cell lines, the use of these anti-CEA antibodies for the diagnosis and therapy of cancer, test kits containing the monoclonal antibodies, and pharmaceutical preparations containing said antibodies.

BACKGROUND OF THE INVENTION

The development of hybridoma technology made it possible to generate cell lines producing monoclonal antibodies (MAbs) of desired specificity which can be used to identify, isolate and characterize biologically important molecules.

The MAbs which are subject of the present invention are directed against carcinoembryonic antigen (CEA). CEA is a complex immunoreactive glycoprotein with a molecular weight of 180,000 found in adenocarcinomas of endodermally derived digestive system epithelia and foetal colon. The role of CEA immunoassays for diagnosis and serially monitoring cancer patients for recurrent disease or response to therapy (Mach et al., Immun. Today 2, 239, 1981; Berche et al., Br. Med. J. 285, 1447, 1982) as well as their use in experimental models of nude mice bearing human colon carcinoma xenografts (Hedin et al., Int. J. Cancer 30, 547, 1982; Buchegger et al., Int. J. Cancer 33, 643, 1984) have been widely evaluated and documented.

One of the major drawbacks of the use of anti-CEA antibodies for clinical purposes has been the cross-reactivity of these antibodies with some apparently normal adult tissues. Previous studies have shown that most conventional hyperimmune antisera raised against different immunogenic forms of CEA cross-react with many different types of carcinomas as well as CEA-related antigens found in normal colonic mucosa, spleen, liver, lung, sweatglands, polymorphonuclear leukocytes and monocytes of apparently normal individuals. The first of the series of identified antigens cross-reacting with CEA was called normal glycoprotein (NGP) or non-specific cross-reacting antigen (NCA) by Mach and Pusztaszeri (Immunochemistry 9, 1031, 1972) and by von Kleist et al. (Proc. Natl. Acad. Sci. 69, 2492, 1972), respectively. Here, it will be referred to as $NCA_{55}$, because it was shown by both research groups to have a molecular weight of about 55 kD. This antigen has also been described by several other research groups under different names, including CCEA-2 (Tuberville et al., Immunochemistry 10, 841, 1973), CCA-III (Primus et al., J. Immunol. 118, 55, 1977) and TEX (Kessler et al., Cancer Res. 38, 1041, 1978). Buchegger et al. (Int. J. Cancer 33, 643, 1984) identified a CEA cross-reacting antigen of 95 kD ($NCA_{95}$). Another antigen very closely related to CEA in terms of cross-reactivity and molecular weight (160 kD) was described by Burtin et al. (in: Fishman & Sell, Onco-developmental gene expression, N.Y. 1976, pp. 609-611) and was designated NCA-II. This antigen appears to be very similar to the normal fecal antigen-2 (NFA-2) described by Matsuoka et al. (Int. J. Cancer 21, 604, 1978). The same group identified in normal adult feces a CEA-related glycoprotein of 20-30 kD called NFA-1 (Kuroki et al., Mol. Immunol. 19, 399, 1982). Finally, biliary glycoprotein-1 (BGP-1) is an antigen cross-reacting with CEA present in normal bile described by Svenberg (Int. J. Cancer 17, 588, 1976). These results as a whole demonstrate that antisera recognize epitopes specific for CEA alone as well as epitopes present on both CEA and CEA-related antigens; they further suggest closely related genes between CEA and CEA-related antigens as well as precursor-product relationships between some of them. According to Hammarström et al. (Proc. Natl. Acad. Sci. 72, 1528, 1975) and Hedin et al. (Mol. Immunol. 23, 1053, 1986) the epitopes are predominantly located on the peptide moieties of CEA and appear to be strongly conformation dependent.

The production of monoclonal anti-CEA antibodies is disclosed by several research groups. Accolla et al. (Proc. Natl. Acad. Sci. 77, 563, 1980) reported that antibodies obtained from two hybridoma clones reacted strongly with CEA but also weakly with NGP. The reactions of these two antibodies with CEA were not competitively inhibited by each other indicating that they react with different antigenic determinants on the CEA molecule. The antibodies described by Kupchik et al. (Cancer Res. 41, 3306, 1981) and Primus et al. (Cancer Res. 43, 686, 1983) have been shown to have at least some degree of reactivity with normal polymorphonuclear leukocytes (PMNs). Kuroki et al. (J. Immunol. 30, 2090, 1984) described two MAbs against CEA which, however, do not react with purified CEA preparations other than those used for immunization. These MAbs have not yet been characterized as to the range of reactivity to tumour versus normal tissues.

OBJECT OF THE INVENTION

Object of the invention are anti-CEA MAbs which have high affinity for CEA, show high percentage of binding to CEA-carrying carcinoma cells, both in vitro and in vivo, and have high tumour to normal tissue (T/N) binding ratios.

DESCRIPTION OF THE INVENTION

The invention concerns a monoclonal antibody specific for human carcinoembryonic antigen (CEA), and derivatives thereof, characterized in that they recognize epitopes of CEA not present on non-specific cross-reacting antigen $NCA_{55}$ or $NCA_{95}$, on biliary glycoprotein, or on granulocytes, and bind to human CEA with an affinity of at least $(1.6\pm0.3)\times10^{10}$ liters/mol. In particular, the invention concerns the monoclonal antibody with the designation MAb CE25, and derivatives thereof.

Derivatives of a monoclonal antibody according to the invention, especially of MAb CE25, are, for example, fragments, such as the univalent fragments Fab or Fab' and the divalent fragment F(ab')$_2$ (Fab = fragment antigen binding), that retain their specificity for the antigenic determinants of CEA, conjugates of the antibody with enzymes, fluorescent markers, metal chelates, cytotoxic or cytostatic substances, avidin, biotin, and the like, and radioactively labelled antibodies.

Enzymes used for antibody conjugates of the invention are, for example, horseradish peroxidase, alkaline phosphatase, $\beta$-D-galactosidase, glucose oxidase, glucoamylase, carbonahydrase, acetylcholinesterase, lysozyme, malate dehydrogenase or glucose-6-phosphate dehydrogenase. Fluorescent markers conjugated with MAb CE25 are fluorescein, fluorochrome, rhodamine, and the like. In such conjugates the antibody is bound to the enzymes or fluorescent markers directly or by the way of a spacer or linker group. Examples for metal chelators are ethylenediaminetetraacetic acid (EDTA), diethylenetriaminepentaacetic acid (DPTA), 1,4,8,11-tetraazatetradecane, 1,4,8,11-tetraazatetradecane-1,4,8,11-tetraacetic acid, 1-oxa-4,7,12,15-tetraazaheptadecane-4,7,12,15-tetraacetic acid, or the like. Cytostatics, applicable in connection with the antibodies of the invention, are, inter alia, alkylating substances, such as mechlorethamine, triethylenephosphoramide, cyclophosphamide, ifosfamide, chlorambucil, busulfan, melphalan or triaziquone, also nitrosourea compounds, such as carmustine, lomustine, or semustine. Also used are antimetabolites, such as methotrexate, mercaptopurine, cytarabine, fluorouracil, floxuridine, or ftorafur. A further group of cytostatics includes vinblastine and vincristine, as well as certain antibiotics, such as actinomycin-D, daunorubicin (=daunomycin), doxorubicin, mithramycin, streptonigrin, mitomycin and bleomycin. Further suitable cytostatics are, inter alia, procarbacine, hydroxyurea, L-asparaginase, dacarbazine, mitotane, estramustine, or podophyllotoxin. Further cytostatic agents are hormones and hormone antagonists, such as corticosteroids, e.g. prednisone, progestins, e.g. hydroxyprogesterone or medroprogesterone, estrogens, e.g. diethylstilbestrol, antiestrogens, e.g. tamoxifen, androgens, e.g. testosterone, and aromatase inhibitors, e.g. aminogluthetimide. Derivatives of a monoclonal antibody of the invention conjugated to a cytotoxic substance contain either the intact toxin or the A-chain derived from it. Toxins suitable for antibody-coupling are, among others, several lectins, such as ricin or abrin, or diphtheria toxin A, and the like.

Radioactively labelled monoclonal antibodies contain e.g. raddioactive iodine ($^{123}I$, $^{125}I$, $^{131}I$), yttrium ($^{90}Y$), technetium ($^{99m}Tc$), or the like.

A monoclonal antibody and derivatives thereof according to the invention are prepared by processes that are known per se, characterized in that hybridoma cells as defined further below secreting the monoclonal antibody are multiplied according to known methods in vitro or in vivo. If desired, the resulting monoclonal antibodies are converted into derivatives thereof.

Multiplication in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growth-sustaining supplements, e.g. feeder cells such as normal mouse peritoneal exudate cells, spleen cells, bone marrow macrophages, or the like.

In vitro production provides relatively pure antibody preparations and allows scale-up to give large amounts of the desired antibodies. Techniques for large scale hybridoma cultivation under tissue culture conditions are known in the art and include homogeneous suspension culture, e.g. in an airlift reactor or in a continuous stirrer reactor, or immobilized or entrapped cell culture, e.g. in hollow fibres, microcapsules, on agarose microbeads or ceramic cartridges.

For isolation of the monoclonal antibodies, the immunoglobulins in the culture supernatants are first concentrated e.g. by precipitation with ammonium sulphate, dialysis against hygroscopic material such as PEG, filtration through selective membranes, or the like. If necessary and/or desired, the concentrated antibodies are purified by the customary chromatography methods, for instance gel filtration, ion-exchange chromatography, chromatography over DEAE-cellulose, Protein A or immunoaffinity chromatography.

Large amounts of the desired monoclonal antibodies can also be obtained by multiplying hybridoma cells in vivo. Cell clones are injected into mammals which are histocompatible with the parent cells, e.g. syngeneic mice, to cause growth of antibody-producing tumours. Optionally, the animals are primed with a hydrocarbon, especially mineral oils such as pristane (tetramethylpentadecane), prior to the injection. After one to three weeks, the desired monoclonal antibodies are recovered from body fluids of said mammal. As an example, hybridoma cells derived from Balb/c mice are intraperitoneally injected into Balb/c mice optionally pretreated with a hydrocarbon such as pristane, and after one to two weeks ascites fluid of these mice is collected. The desired monoclonal antibodies are isolated from the body fluids by conventional methods as described above.

Fragments of monoclonal antibodies, for example Fab, Fab' or F(ab')$_2$ fragments, which retain their specifity towards human CEA, can be obtained from the antibody prepared as described above by methods known per se, e.g. by digestion with enzymes such as pepsin or papain and/or cleavage of disulfide bonds by chemical reduction.

Conjugates of monoclonal antibodies of the invention are prepared by methods known in the art, e.g. by reacting a monoclonal antibody prepared as described hereinbefore with the enzyme in the presence of a coupling agent, e.g. glutaraldehyde, periodate, N,N'-o-phenylenedimaleimide, N-(m-maleimidobenzoyloxy)-succinimide, N-(3-[2'-pyridyldithio]-propionoxy)-succinimide, N-ethyl-N'-(3-dimethylaminopropyl)-carbodiimide or the like. Conjugates with avidin are prepared likewise. Conjugates with biotin are prepared e.g. by reacting monoclonal antibodies with an activated ester of biotin such as the biotin N-hydroxysuccinimide ester. Conjugates with fluorescent markers are prepared in the presence of a coupling agent, e.g. those listed above, or by reaction with an isothiocyanate, preferably fluorescein-isothiocyanate. Antibody-conjugates with metal chelates are prepared in an analogous manner.

Monoclonal antibodies radioactively labelled with iodine ($^{123}I$, $^{125}I$, $^{131}I$) are obtained from the monoclonal antibodies according to the invention by iodination known per se, for example with radioactive sodium or potassium iodide and a chemical oxidising agent, such as sodium hypochlorite, chloramine T or the like, or an enzymatic oxidising agent, such as lactoperoxidase, glucose oxidase and glucose. Monoclonal antibodies according to the invention are coupled to yttrium ($^{90}Y$) for example by diethylene-triaminepentaacetic acid (DPTA)-chelation. Technetium-99m labelled antibodies are prepared by ligand exchange processes, for example by reducing pertechnate (TcO$_4^-$) with stannous solution, chelating the reduced technetium onto a Sephadex column and applying the antibody to this column, or by direct labelling techniques, e.g. by incubating pertechnate, a reducing agent such as SnCl$_2$, a buffer solution such as a sodium-potassium phthalate-solution, and the antibody.

The invention also concerns a hybridoma cell line which secretes a monoclonal anti-CEA antibody according to the invention, preferably the hybridoma cell line with the designation CE25, which was deposited at the "Collection Nationale de Cultures de Microorganismes" of the Institut Pasteur, Paris, on Dec. 15, 1987, under the number I-719.

The hybridoma cell lines of the invention are genetically stable, secrete monoclonal antibodies of the invention of constant specificity and can be activated from deep-frozen cultures by thawing and recloning.

The invention also concerns a process for the preparation of such a hybridoma cell line, characterized in that Balb/c mice are immunized with purified human CEA or with an antigenic carrier containing purified human CEA, antibody-producing cells of the immunized Balb/c mice are fused with cells of the myeloma P3-NS2/1Ag4, the hybrid cells obtained in the fusion are cloned, and cell clones secreting the desired antibodies are selected.

Immunization with high-purity CEA, prepared by the following methods, is preferred. CEA is extracted from CEA-carrying cells, for example metastases of colorectal or lung adenocarcinoma or primary lung adenocarcinoma, by precipitation with perchloric acid or by saline-extraction. The latter method is advantageous since the resulting CEA is less denatured. For the saline-extraction procedure, CEA-carrying tissue is homogenized in buffer of pH-range 7.0–7.6 such as phosphate buffer, Tris-buffer, TAPSO buffer ([3-[N-tris(hydroxymethyl)methylamino]-2-hydroxypropanesulfonic acid), POPSO buffer (piperazine-N,N'-bis[2-hydroxypropanesulfonic acid]), EPPS buffer (N-[2-hydroxyethyl]-piperazine-N'-3-propanesulfonic acid), or the like. Homogenization is achieved by methods known per se, for example by the use of mechanical devices, e.g. a mixer, blendor or ultraturrax, by ultrasound waves, by the addition of surface-active compounds such as Tween, Triton or Tergitol, and the like. The extracted CEA is purified by conventional chromatography methods such as ion-exchange chromatography, gel-filtration, affinity chromatography, or the like, and/or by application to an immunoadsorbent consisting of a combination of known anti-CEA antibodies conjugated to a matrix such as sepharose or agarose, optionally activated, e.g. with cyanogen bromide, nitrophenyl chloroformate, polyacrylamide hydrazide or others.

Especially preferred is a process for the preparation of the hybridoma cell lines of the invention and derivatives thereof, characterized in that Balb/c mice are immunized by injecting 15 μg of saline-extracted purified CEA intraperitoneally, a series of booster injections with 15, 50 and 150 μg of saline-extracted purified CEA is given after 4 months intraperitoneally, spleen cells are taken from the immunized animals 3 days after the last injection and fused with cells of the myeloma P3-NS2/1Ag4 in the presence of a fusion promoter. Fusion promoters considered are e.g. Sendai virus or other paramyxoviruses, optionally in UV-inactivated form, calcium ions, surface-active lipids such as lysolecithin, or polyethylene glycol. Cell fusion is accomplished according to previously described methods (Köhler & Milstein, Nature 256, 495, 1975). Preferentially, the myeloma cells are fused with a three-to twentyfold excess of spleen cells from immunized mammals in a solution containing about 30% to about 60% polyethylene glycol of a molecular weight between 1000 and 4000.

After the fusion, the cells are resuspended and expanded in suitable culture media as described hereinbefore, supplemented with a selective medium, for example HAT medium, at regular intervals in order to prevent normal myeloma cells from overgrowing the hybridoma cells.

The hybridoma cell culture supernatants are screened for the monoclonal antibody to CEA with an immunoassay, preferentially with an enzyme immunoassay or a radioimmunoassay. Hybridoma cell lines secreting monoclonal anti-CEA MAbs as described above, for example the cell line CE25 secreting MAb CE25, are cloned, e.g. by limiting dilution or in soft agar, preferentially twice or more. Optionally, hybridoma cells are passaged through animals, e.g. mice, by intraperitoneal injection and harvesting of ascites, which stabilizes hybridomas and improves growth characteristics. The cloned cell lines may be frozen in a conventional manner.

The monoclonal antibodies and derivatives thereof according to the invention are useful in the diagnosis of cancer.

An example of diagnostic use is the qualitative and quantitative determination of human carcinoembryonic antigen, especially in biological fluids. The monoclonal antibody of the invention and derivatives thereof may be used in any of the immunoassays known per se that utilize the binding interactions between antigen and monoclonal antibody, such as radioimmunoassays (RIA), enzyme-linked immunoassays, immunofluorescence tests, latex agglutination or haemagglutination.

The monoclonal antibodies according to the invention can be used as such or in the form of radioactively labelled derivatives in a radioimmunoassay (RIA). Any of the known modifications of a RIA can be used, for example RIA in homogeneous phase, solid phase RIA or heterogeneous RIA, single RIA or double (sandwich) RIA with direct or indirect (competitive) determination of CEA. There is preferred a sandwich RIA in which a suitable carrier, for example the plastics surface of a microtitre plate or of a test tube, for example of polystyrene, polypropylene or polyvinyl chloride, glass or plastics beads, filter paper, or dextran, cellulose acetate or nitrocellulose sheets or the like, is coated with a monoclonal antibody to CEA by simple adsorption or optionally after activation of the carrier, for example with glutaraldehyde or cyanogen bromide, and incubated with the test solution and a solution of a monoclonal antibody radioactively labelled with $^{125}$I, the dissolved monoclonal antibody recognizing another epitope of CEA than the carrier-bound monoclonal antibody, and the amount of CEA is determined by measuring the radioactivity bound to the carrier. One of the antibodies employed in the sandwich RIA is a monoclonal anti-CEA antibody of the invention.

Particularly preferred is a sandwich radioimmunoassay as described hereinbefore, wherein a monoclonal antibody of the inveniton is bound to a bead, for example a polystyrene bead, this coated bead is incubated in a test or standard solution containing CEA and is finally developed with a radiolabelled monoclonal antibody recognizing a different epitope.

The monoclonal antibodies according to the invention can be used as such or in the form of enzyme-conjugated derivatives in an enzyme-immunoassay. Such immunoassays include test procedures in which enzyme-labelled monoclonal antibody derivatives according to the invention or enzyme-labelled antibodies known per se that recognize and bind an epitope of the antibodies of the invention are used.

There is preferred an ELISA (enzyme-linked immunosorbent assay) in which a carrier as described above for a RIA is coated with a monoclonal antibody according to the invention, incubated with a test solution containing CEA and then with a polyclonal serum to CEA, for example sheep serum, and, finally, the bound antibodies of the polyclonal serum are developed by enzyme-labelled antibodies that recognize and bind to them, and the amount of the protein bound is determined by an enzyme substrate reaction. Such an enzyme-labelled antibody is, for example, a phosphatase-labelled goat-anti-sheep immunoglobulin.

There is also preferred an ELISA in which a carrier coated with a monoclonal antibody according to the invention is incubated with a test solution and with a solution of a monoclonal antibody that is conjugated with an enzyme, the dissolved monoclonal antibody recognizing a different epitope of CEA than does the carrier-bound monoclonal antibody. By an enzyme substrate reaction that results, for example, in a colour change and can be observed by eye or with optical measuring devices, the amount of bound enzyme, which is proportional to the amount of CEA in the test solution, is measured.

There is also preferred an ELISA in which an enzyme-labelled monoclonal antibody according to the invention is used and the carrier is coated with a monoclonal anti-CEA antibody recognizing a different epitope than the monoclonal antibody according to the invention.

Particularly preferred is an enzyme immunoassay called immunodot analysis, in which test or standard solutions containing CEA are spotted on a microporous carrier with high intrinsic affinity for polypeptides, e.g. on nitrocellulose, the carrier bearing one or several dots of said samples is incubated in a solution of a monoclonal antibody of the invention, then in a solution of an enzyme-labelled second antibody that recognizes and binds the monoclonal antibody of the invention and finally in a solution of an enzyme substrate which leads to a detectable signal, e.g. a coloured substance. Such an enzyme-labelled second antibody is e.g. rabbit-anti-mouse immunoglobulin conjugated with horseradish peroxidase which can be developed with suitable enzyme substrates such as 4-chloro-1-naphthol or the like.

The monoclonal antibodies according to the invention can be used as such or in the form of derivatives according to the invention conjugated with fluorescent markers in immunofluorescence tests. Such immunofluorescence tests include procedures wherein monoclonal antibody derivatives according to the invention, e.g. derivatives conjugated with fluorescein, or fluorescent marker-labelled antibodies known per se that recognize and bind an epitope of the monoclonal antibody of the invention are used.

There is preferred an immunofluorescence test in which a carrier as described above for a RIA is coated according to standard methods with cells to be tested for the presence of CEA, the cells are fixed and permeabilized to allow interaction of proteinaceous material inside the cell with solutions applied, then incubated with a solution of a monoclonal antibody derivative conjugated with a fluorescent marker, or incubated with a solution of a monoclonal antibody of the invention followed by a solution of a fluorescent marker-labelled second antibody that recognizes and binds the monoclonal antibody of the invention, e.g. a fluorescein-labelled rabbit-anti-mouse immunoglobulin. The presence of CEA is then detected and localized by standard fluorescence microscopy or flow cytometry.

The use according to the invention of monoclonal antibodies and derivatives thereof as described hereinbefore for the qualitative and quantitative determination of human CEA also includes other immunoassays known per se, for example latex agglutination with antibody-coated or antigen-coated latex particles or hemagglutination with antibody-coated or antigen-coated red blood corpuscles or the like.

The invention relates also to test kits for the qualitative and quantitative determination of human CEA containing monoclonal antibodies of the invention and/or derivatives thereof and, optionally, other monoclonal or polyclonal antibodies and/or adjuncts.

Test kits according to the invention for a radioimmunoassay contain, for example, a suitable carrier, uncoated or coated with a monoclonal antibody of the invention, optionally freeze-dried or concentrated solutions of a monoclonal or polyclonal antibody to CEA and/or a radio-labelled derivative thereof, standard CEA-solutions, buffer solutions and, optionally, polypeptides and detergents for preventing non-specific adsorption and aggregate formation, pipettes, reaction vessels, calibration curves, instruction manuals and the like.

Test kits according to the invention for an enzyme immunoassay contain, for example, a suitable carrier, e.g. microtiter plates or nitrocellulose sheets, optionally freeze-dried or concentrated solutions of a monoclonal antibody of the invention and of an enzyme-labelled monoclonal or polyclonal antibody to CEA or to a first antibody recognizing CEA, enzyme substrates in solid or dissolved form, standard CEA-solutions, buffer solutions and, optionally, polypeptides and detergents, pipettes, reaction vessels, calibration curves, colour scale tables, instruction manuals and the like.

Test kits according to the invention for an immunofluorescence test contain, for example, a suitable carrier, e.g. plastic coverslips or glass slides, optionally freeze-dried or concentrated solutions of a monoclonal antibody of the invention and of a fluorescein-labelled polyclonal antibody recognizing the monoclonal antibody, buffer solutions and, optionally, standard CEA-solutions, polypeptides and detergents, pipettes, reaction vessels, instruction manuals and the like.

In addition, the monoclonal antibody of the invention and derivatives thereof are used for localization and in vivo imaging of tumours. For in vivo imaging, the monoclonal antibody of the invention is radio-labelled or conjugated to a metal chelate complexing a radionuclide, e.g. iodine, technetium, rhenium, or the like, and radioscanning techniques are used to detect primary and metastatic tumours. To that end, the radioactive antibody is injected e.g. intravenously and the patient scanned with a gamma imager at regular intervals. Tumours expressing CEA will take up more radioactive antibodies than other tissue and will be clearly recognized by the gamma imaging camera. Preferentially monoclonal antibodies labelled with $^{131}I$ or $^{123}I$ are used for radioscanning in amounts of 3 to 50 μg representing 15 to 30 μCi per kg body weight. For biocidal activity in the treatment of cancer, the antibodies of the invention are used as derivatives conjugated to cytostatic or cytotoxic substances as described hereinbefore, e.g. ricin A, as radiolabelled derivatives, or else delivered in liposomes containing biocidal reagents. The therapeutic dose for mammals is between approximatively 1 mg and 5 mg per kg body weight for monoclonal antibodies themselves, and between 0.1 mg and 5 mg per kg body weight for conjugates with cytotoxic drugs, depending on the status of the patient and the mode of application.

The invention also relates to pharmaceutical preparations containing the monoclonal antibody of the invention and/or derivatives thereof with a high specificity for CEA as disclosed hereinbefore. The pharmaceutical preparations contain, for example, the monoclonal antibody of the invention or derivatives thereof in an effective amount together or in admixture with inorganic or organic, solid or liquid pharmaceutically acceptable carriers.

Preferred are pharmaceutical preparations for parenteral application. Preparations for intramuscular, subcutaneous or intravenous application are e.g. isotonic aqueous solutions or suspensions, optionally prepared shortly before use from lyophilized or concentrated preparations. The pharmaceutical preparations may be sterilized and contain adjuvants e.g. for conserving, stabilizing, wetting, emulsifying or solubilizing the ingredients, salts for the regulation of the osmotic pressure, buffer and/or compounds regulating the viscosity, e.g. sodium carboxycellulose, dextran, polyvinylpyrrolidone or gelatine. They are prepared by methods known in the art, e.g. by conventional mixing, dissolving or lyophilizing, and contain from approximately 0.01% to approximately 50% of active ingredients. The preparations for injections are processed, filled into ampoules or vials, and sealed under aseptic conditions according to methods known in the art.

The following examples illustrate the invention but do not limit it to any extent.

Abbreviations

| | |
|---|---|
| BSA | bovine serum albumin |
| FCS | foetal calf serum |
| ELISA | enzyme-linked immunosorbent assay |
| HAT medium | hypoxanthine/aminopterin/thymidine medium |
| NCA | non-specific cross-reacting antigen |
| PBS | phosphate buffered saline |

EXAMPLE 1

Preparation of Hybridoma Cell Line CE25

1.1 Purification of Carcinoembryonic Antigen (CEA)

Colon carcinoma liver metastases obtained from autopsies (within 6 h of death) are extracted with saline. 1 vol. of tissue is first homogenized in 3 vol. of 0.02M phosphate buffer pH 7.4 at 4° C. for 10 min in a Sorvall Omnimixer at 8,000 rpm. The crude homogenate is then centrifuged at 8,000 g for 15 min at 4° C. The clear supernatant is applied to an immunoadsorbent consisting of a pool of the known anti-CEA monoclonal antibodies MAb 35 and MAb 115 (Haskell et al., Cancer Res. 43, 3857, 1983; Buchegger et al., J. Exp. Med. 158, 413, 1983) and MAb 73 (Buchegger et al., Immunol. Letters 5, 85, 1982) coupled to CNBr-activated Sepharose. CEA is eluted with 2M ammonium thiocyanate. After a final Sepharose 6B chromatography CEA is obtained at 90% purity.

1.2 Immunization of Balb/c Mice

Balb/c mice two months of age are immunized with CEA by injecting intraperitoneally 15 µg of saline-extracted purified CEA with complete Freund's adjuvant. After 4 months, a series of booster injections is given comprising 15, 50 and 150 µg of the same saline CEA preparation without Freund's adjuvant given intraperitoneally 5, 4 and 3 days before fusion, respectively.

1.3 Cell Fusion

Cell fusion is accomplished using $1.5 \times 10^8$ spleen cells of immunized mice and $1.5 \times 10^7$ cells from the mouse myeloma P3-NS2/1Ag4 according to conventional previously described methods (Koehler & Milstein, Nature 256, 495, 1975). After washing, the cells are resuspended in 48 ml of standard Dulbecco's minimum essential medium (Gibco No. 0422501). $3 \times 10^6$ normal mouse peritoneal exudate cells per fusion are added as feeder cells. The cells are distributed into $96 \times 0.5$ ml Costar wells and fed 3 times per week with standard HAT selection medium for 3-6 weeks. When the growth of hybridoma cells becomes visible, the supernatants are screened as described in Example 1.4. Positive hybridomas are recloned and stored.

1.4 Antibody detection assay

Culture fluids of growing hybridomas are tested for the presence of anti-CEA antibody by a modification of the assay of Farr (J. Infect. Dis. 103, 239, 1958) as described previously (Accolla et al., Proc. Natl. Acad. Sci. 77, 563, 1980). 1:10 (v/v) dilutions of cell culture supernatants are incubated in duplicate with $^{125}$I-labelled CEA in 0.02M Tris-HCl buffer, pH 7.4. CEA bound to antibodies is precipitated at 4° C. by adding cold, saturated ammonium sulphate solution in the presence of normal human serum.

Hybridoma cell lines secreting anti-CEA antibodies which recognize epitopes of CEA not present on non-specific cross-reacting antigen $NCA_{55}$ or $NCA_{95}$, on biliary glycoprotein or on granulocytes, and bind to human CEA with an affinity of at least $(1.6 \pm 0.3) \times 10^{10}$ liters/mol, for example cell line CE25 secreting MAb CE25, are selected for further studies.

1.5 HYBRIDOMA STORAGE AND PROCESSING

The selected hybridoma cells can be grown in culture, frozen at −80° C. or in liquid nitrogen and then reactivated. The cells are cloned by the method of limiting dilution and expanded by forming ascites in Balb/c mice primed with pristane. Cell line CE25 was deposited at the "Collection Nationale de Cultures de Microorganismes" of the Institut Pasteur, Paris, on Dec. 15, 1987, under the number I-719.

EXAMPLE 2

Isolation and Purification of the Monoclonal Antibody MAb CE25 and Preparation of Derivatives 2.1 In vivo-Synthesis Balb/c mice 8-10 weeks of age are pretreated intraperitoneally with 0.5 ml pristane (Aldrich). 1-3 weeks later, $2-5 \times 10^6$ cloned hybridoma cells are inoculated intraperitoneally. After 8-10 days ascites fluid is collected, centrifuged at $800 \times g$ and stored at −20° C. or at −80° C.

Defrosted ascites fluid is centrifuged at $50,000 \times g$ for 60 min. A fat layer floating on the surface is carefully removed, and the protein concentration is adjusted to a concentration of 10-12 mg/ml. Crude immunoglobulin is precipitated by dropwise addition of 0.9 volume equivalents of saturated ammonium sulphate at 0° C., then dissolved in 0.04M phosphate buffer pH 8 and dialyzed against the same buffer. An immunologically active immunoglobulin fraction is obtained by DEAE-D52 cellulose (Whatman) chromatography where MAb CE25 elutes in the void volume. Such preparations yielding between 5 and 15 mg antibody per ml ascites can be used directly or antibody fragments can be prepared for in vitro and in vivo application (Example 2.3).

2.2 In vitro-Synthesis

A preculture of cell line CE25 is obtained by culturing hybridoma cells at physiological temperature (around 37° C.) in RPMI 1640 medium containing 10% FCS to a final cell density of $5 \times 10^5$ to $10^6$ cells per ml. The whole preculture is filled into Bellco culture vessels and adjusted to a total volume of 1500 ml with fresh RPMI 1640 medium/10% FCS. The culture is stirred at around 37° C. under 5% $CO_2$ at 30 rpm for two to three days, then diluted to a total volume of 3000 ml with RPMI 1640/10% FCS and stirred for another seven to ten days. After this time 95% of the cells are dead. The culture broth is centrifuged at $1000 \times g$ for 20 min at 4° C. The supernatant is filtered through a filter with pore size 0.2 μm under sterile conditions. Crude immunoglobulin is precipitated by slow dropwise addition of 0.9 volume equivalents of saturated ammonium sulphate at 0° C. This precipitate is purified as described in Example 2.1.

2.3 FRAGMENT PREPARATION

F(ab')$_2$ fragments of MAb CE25 are prepared using pepsin (2-4%, w/w) digestion in 0.2M acetate buffer pH 4 for 22 h at 37° C. (Lamyoi & Nisonoff, J. Immunol.Methods 56, 235, 1983). F(ab')$_2$ fragments are purified by Sephadex G150 chromatography where the 100 kD F(ab')$_2$ fragments elute as a single peak and the small digestion products are well separated. Control mouse IgG$_1$ and F(ab')$_2$ fragments are purified by identical methods from ascites of mice injected with $P3 \times 63$ myeloma cells (Koehler & Milstein, Nature 256, 495, 1975). SDS-polyacrylamide gel electrophoresis according to Laemmli (Nature 227, 680, 1970) reveals more than 95% purity of IgG and F(ab')$_2$ fractions.

2.4 Radiolabelling of MAb CE25 and its Fragments

MAb CE25 or fragments are labelled with $^{131}$I by the chloramine-T method to yield specific activities of 8-9 μCi/μg protein. No preferential labelling of intact MAbs compared to fragments is observed. Protein bound iodine is separated from free iodine by Sephadex chromatography, which reveals the presence of less than 1% $^{131}$I bound to aggregated proteins. Immunoreactivity is controlled by incubation of CEA bound to CNBr-activated Sepharose (Pharmacia).

EXAMPLE 3

Characterization of Monoclonal Antibody MAb CE25

3.1 Determination of Class and Subclass of MAb CE25

The class and subclass of monoclonal antibody MAb CE25 produced by cloned hybridoma cells is determined by the known agar-gel immunodiffusion technique of Ouchterlony using class and subclass specific rabbit antibodies (Bionetics). The results are confirmed by an enzyme immunoassay (ELISA) in the following way: Microtiter plates are coated with 1 μg per well of a rabbit immunoglobulin preparation of a class- or subclass-specific serum (Bionetics) in 50 μl of PBS. Free binding capacity of the plate is saturated with a buffer of 1% bovine serum albumin in PBS containing 0.2% $NaN_3$ (w/v), pH 7.4. 100 μl probes containing monoclonal antibodies are incubated in the wells at 37° C. for 1 h. The plates are washed with PBS, then incubated at 37° C. for 1 h with a phosphatase conjugated rabbit immunoglobulin preparation of the same specificity as used for coating the plates. The fixed enzyme is developed by incubating (37° C., 30 min) with a solution of the enzyme substrated p-nitrophenyl phosphate (1 mg/ml in diethanolamine buffer 10% containing 0.5 mM $MgCl_2$ and 0.02% (w/v) $NaN_3$, pH 9.8) and measuring the optical density at 405 nm. The monoclonal antibody MAb CE25 is of class IgG1.

3.2 CROSS-REACTIVITY WITH NORMAL TISSUE ANTIGENS

Hybridoma cell line CE25 supernatant is tested for cross-reactivity with granulocytes present in frozen sections of normal spleen, pancreas, lung and liver, by indirect immunoperoxidase staining. In addition, the absence of cross-reaction with biliary glycoprotein is determined on normal human liver tissue sections. For antigen staining with anti-CEA MAb a threelayer biotin-avidin-peroxidase technique is used (Guesdon et al., J. Histochem.Cytochem. 27, 1131, 1979). Briefly, 10 μm cryostat sections are fixed for 10 minutes in acetone at room temperature, washed in cold PBS containing $5 \times 10^{-5}$M thimerosal and treated with 7% $H_2O_2$ to abolish endogenous peroxidase activity. The sections are then each incubated for 60 min with 25 μl of undiluted culture fluid from the anti-CEA hybridoma or from the myeloma cell line $P3 \times 63Ag8$ used as control. The second incubation, of 15 min, is with biotinylated horse-anti-mouse IgG antibody, followed by a third incubation, of 15 min, with the avidin-peroxidase conjugate (Vector Laboratories, Burlingame, CA, USA). All incubations are performed at room temperature and followed by a wash with PBS. Finally, the peroxidase activity is revealed by adding a freshly prepared solution containing 0.4% 3-amino-9-ethyl-carbazole and 0.015% $H_2O_2$, and the tissues are counterstained with hematoxylin (Schreyer et al., in: Sordat, 4th Int. Workshop on immune-deficient animals in experimental research, Basel 1984).

The results are summarized in the following table:

| immunoperoxidase on | staining result |
| --- | --- |
| colon carcinoma | ++ |
| normal pancreas (pancreatic ducts) | — |
| normal liver (bile ducts) | — |
| normal lung (epithelial cells) | (+) |
| spleen granulocytes | — | symbols: + + strongly positive staining, (+) occasional staining of a few alveolar epithelial cells, —no staining The specificity of MAb CE25 is further analyzed by a radioimmunoassay using purified radiolabelled non-specific cross-reacting antigens NCA$_{55}$ and NCA$_{95}$. The study is conducted as described in example 1.4 for the Farr assay except that $^{125}$I-labelled NCA is substituted for $^{125}$I-labelled CEA.

NCA is purified from a perchloric acid extract of normal lung by filtration on Sephadex G-200 followed by immunoadsorption on a CNBr-Sepharose 4B column containing IgG from a goat anti-CEA antiserum with known cross-reaction to NCA (Heumann et al., in: Lehmann, Carcino-embryonic proteins, Vol. 11, Amsterdam 1979). $NCA_{95}$ and $NCA_{55}$ are further purified by immunoadsorbent columns containing MAbs recognizing each one of these two NCA (Buchegger et al., Int. J. Cancer 33, 643, 1984). $NCA_{95}$ is labelled with $^{125}I$ by the chloramine T-method, $NCA_{55}$ is $^{125}I$-labelled with the Balton and Hunter reagent (Amersham, Bucks., England).

The test results are:

| radioimmunoassay on | percentage of radio-labelled antigen precipitated |
|---|---|
| $^{125}I$ CEA | 54 |
| $^{125}I$ $NCA_{55}$ | 0 |
| $^{125}I$ $NCA_{95}$ | 1 |

Furthermore binding of $^{125}I$-labelled MAb CE25 to CEA bound to CNBr-activated Sepharose and to glutaraldehyde fixed colon tumour cells Co 112 after overnight incubation at 25° C. and binding to packed, freshly prepared human leukocytes after 4 hours incubation at 4° C. is measured.

The results are given below:

| $^{125}I$ MAb binding to | percentage of input radiolabelled MAb |
|---|---|
| CEA immobilized on CNBr-Sepharose | 75 |
| fixed Co 112 cells | 60 |
| fresh granulocytes | <1.7 |

The above-given results indicate that MAb CE25 is a good candidate for optimal tumour localization together with minimal, non-specific accumulation in bone marrow and liver.

3.3 Determination of Affinity Constants

To a limited amount of MAb CE25, increasing amounts of $^{125}I$-labelled CEA are added in PBS as described by Accolla et al. (Proc.Natl.Acad. Sci. 77, 563,1980). After 16 hours, normal human serum is added followed by cold saturated ammonium sulphate to precipitate CEA bound to antibodies. The radioactivity of the total sample and of the precipitate is determined by γ-counting.

To calculate the affinity constant, saturation curves obtained at equilibrium are transformed and analyzed by Scatchard plot (Ann.N.Y.Acad.Sci. 51, 660, 1949).

MAb CE25 binds to human CEA with an affinity of at least $(1.6\pm0.3)\times10^{10}$ liters/mol.

3.4 Determination of Epitope Recognized by MAb CE25

The antigenic determinant (epitope) of CEA recognized by MAb CE25 is assessed by a cross-inhibition technique in which $^{125}I$-labelled MAb CE25 is tested for its binding capacity to unlabelled CEA following incubation with a 1000 fold excess of other anti-CEA MAbs, as described previously by Accolla et al. (Proc.-Natl.Acad.Sci. 77, 563, 1980) and Haskell et al. (Cancer Res. 43, 3857, 1983). The results indicate that MAb CE25 has a unique specificity for a CEA epitope not recognized by any of the previously published anti-CEA MAb.

Compared to the epitope specificity of MAbs previously described by Buchegger et al. (Int.J.Cancer 33, 643, 1984), the epitope recognized by MAb CE25 is sterically in close relation to an epitope recognized by the known MAb 202. Binding of MAb CE25 is strongly inhibited by MAb 202. The two epitopes are clearly different, however, because MAb 202 shows strong cross-reaction with granulocytes which is completely absent for MAb CE25.

The epitope recognized by MAb CE25 on the CEA molecule is either repetitive or better accessible to the monoclonal antibody than epitopes recognized by other anti-CEA MAbs. This is suggested by binding assays where radiolabelled MAb CE25 (1 ng) is incubated with living colon carcinoma cells ($3\times10^6$ cells). In this test, MAb CE25 binds up to 36% while the known anti-CEA MAbs 35 and MAb 73 bind to less than 16%.

These results are confirmed by further binding assays where increasing amounts of MAb CE25 and the well characterized and highly specific MAb 35 are incubated either with purified CEA bound to CNBr-activated Sepharose or with living colon carcinoma cells as described in the following.

For binding assays to CEA-Sepharose, increasing concentrations of the two radiolabelled monoclonal antibodies (0.15-40 μg) are incubated for 16 h at 25° C. with 3 μg CEA bound to Sepharose-CNBr. Non-specific binding is determined by incubation with Sepharose-CNBr containing irrelevant protein and is substracted. The results demonstrate that about 4 times more MAb CE25 binds to Sepharose-bound CEA than MAb 35.

Very similar results are obtained in an assay with living colon carcinoma cells. The colon carcinoma cells are grown on 96 well tissue culture plates. After washing, increasing amounts of radiolabelled MAbs (2-450 ng) are then incubated with the adherent cells for 4 h at 37° C. in culture medium. Non-specific binding is determined by using high amounts of unlabelled MAb to inhibit specific binding and is substracted. As in the CEA-Sepharose assay described above, 4 times higher binding of MAb CE25 to the colon carcinoma cells is obtained compared to MAb 35.

Thus, the superior binding of MAb CE25 to CEA-expressing cells makes the antibody a promising candidate for diagnostic and therapeutic application.

EXAMPLE 4

Immunoscintigraphy in Nude Mice

4.1 Nude Mouse Tumor Models

The human colon carcinoma T380 (Martin & Halpern, Cancer Res. 44, 5475, 1984; Mach et al., Nature 248, 704, 1974) serially transplanted subcutaneously into nude mice (Iffa Credo, Arbesle, France), is used as target for radiolabelled anti-CEA MAbs and fragments. Tumor T380 shows relatively few necrotic areas up to sizes of more than 1 g due to a high degree of vascularization. The tumour is moderately differentiated and contains numerous pseudolumina which are rich of CEA, surrounded by epithelial cells whith a lower degree of organization. CEA production and release into the blood stream have been described. 15 to 45 μg CEA can be extracted per gram tumour, and 10 to 18 ng CEA per hour are produced and released into blood from a 1 g tumour (Martin and Halpern, Cancer Res. 44, 5475, 1984).

4.2 Analytic Injection of Tumour Bearing Nude Mice

MAb CE25, MAb 35 and MAb B17, each recognizing different epitopes of the CEA molecule, and their F(ab')$_2$ fragments are radiolabelled with $^{131}$I by the chloramine-T method, giving a final specific activity of 8-9 μCi/μg protein, and intravenously injected into groups of 3-4 nude mice bearing colon tumours T380 of 0.2 to 1.5 gram. Mixtures of antibodies and their fragments are used to achieve good and rapid penetration of tumour nodules as well as delivery of high amounts of antibodies for a longer period of time. Fragments and intact $^{131}$I-labelled antibodies can also irradiate different areas of tumour nodules. Labelling with $^{131}$I is also advantageous in view of good tumour penetration. The mice are dissected 3 days after injection of intact antibodies or 2 days after injection of F(ab')$_2$. Tumour to normal tissue ratios (T/N) are calculated as well as a tumour to whole body ratio (T/N mean). "T/N mean" expresses the ratio of tumour radioactivity/g compared with the whole body radioactivity/g including all organs and dissected carcass.

Results are summarized in the table below:

$$\text{volume} = r1 \times r2 \times r3 \times 4/3\pi \, (r = \text{radius})$$

tumour volumes are calculated. Precision for individual tumour size measurements is about ±10% as estimated from measurements by different people. Whole body counting using a RADX Assayer 1 (RADX Corporation, Houston, Texas) allows determination of 2 half lifes. The whole body radiation dose is then calculated by the formulas $$D_{62} = 2.13 \times T.\mathit{eff} \times 1.44 \times C \times E_\beta \, \text{rads}$$

(T.eff in hours, C in μCi/g, $E_\beta = 0.19$ for $^{131}$I) and $$D_\gamma = 2.13 \times T.\mathit{eff} \times 1.44 \times C \times \sum_{i=1}^{N} f_i \times E_i \times \phi \, (u_{en}r)_i \, \text{rads}$$

(f = frequency of γ-rays, E = energy of γ-rays, φ = linear absorption coefficient ($u_{en}$) multiplied by the radius (r), see Johns and Cunningham, in: Friedman, Monograph in the Bannerstane Division of American lectures on Radiation Therapy, Springfield 1978)

The whole body radiation dose for the mouse is due to 90% to $\beta^-$ radiation and to 10% to γ radiation. Mice

| Dissection time | Tumour size in g | % injected dose per g tumour* | Tumour to normal tissue ratios | | | | | | | |
|---|---|---|---|---|---|---|---|---|---|---|
| | | | T/N mean** | T/blood | T/liver | T/kidney | T/lung | T/spleen | T/bone | T/muscle |
| 24 h | 0.34 | 25.5 | 26.7 | 7.2 | 12.6 | 14.2 | 10.6 | 20.1 | 40.1 | 79.6 |
| 72 h | 0.27 | 7.2 | 22.2 | 4.7 | 13.3 | 14.8 | 7.0 | 15.3 | 29.4 | 58.4 |
| 168 h | 0.21 | 2.2 | 13.2 | 2.4 | 11.9 | 8.8 | 3.3 | 8.1 | 19.4 | 26.6 |

T/N ratios in mice dissected after injection of therapeutic doses of $^{131}$I anti-CEA MAbs and fragments

*Percent of injected radioactivity per gram of tumour measured at different times (uncorrected for physical half life).
**"T/N mean" gives the ratio of radioactivity per gram tumour as compared to the whole mouse (without tumour) including blood and carcass.

4.3 Therapeutic Injection of Nude Mice Bearing Colon Tumour T380

To demonstrate the possibility of obtaining tumour regression of human colon carcinomas by injection of $^{131}$I-labelled anti-CEA MAbs, the following experiments are carried out.

For therapy, intact antibodies are mixed with their F(ab')$_2$ fragments in a ratio of 1:2. One mg of this mixture is labelled by chloramine T with 10 mCi of $^{131}$I to a specific activity of 8 μCi/μg protein. Male nude mice 7 weeks of age are transplanted with colon tumour T380 and 3-4 mice are randomly distributed to each cage. Tumours are measured three days before and at day of radiolabel injection, i.e. 10 days after transplantation when the tumours are well established and organized and in exponential growth. 4 groups of mice are chosen with growing tumours of variable sizes. The first group is intravenously injected with 600 μCi $^{131}$I labelled antibodies, the second with 600 μCi $^{131}$I labelled normal IgG (also intact and F(ab')$_2$ mixed). A third group is injected with a corresponding amount of 75 μg unlabelled anti-CEA antibodies, and a fourth group is not injected at all. The thyroid of the mice injected with $^{131}$I labelled proteins is protected by adding 5% Lugol solution into the drinking water (0.5 ml per 300 ml water) starting 3 days before injection and up to 6 weeks thereafter. The mice are held in aseptic conditions using filter paper topped cages and access limited to 2 people. Initially, all 3 to 4 days, and later on once a week, tumour diameters in the 3 dimensions are measured. By using the formula dissected at 24 and 72 hours and at day 7 from injection of radiolabelled MAb in therapeutic dose are analyzed for T/N ratios. An overall mean T/N ratio is calculated from the tumour to whole body ratios in these animals taking a putative tumour radioactivity enrichment and decrease phase in account. A tumour dose due to $\beta^-$ radiation only is calculated as compared to the whole body dose. The tumours are examined histologically at 1, 3 and 7 days, and autoradiography is obtained from tumours dissected at 24 and 72 hours after injection. Immunoperoxidase staining using pig anti-CEA MAbs and anti-pig IgG-peroxidase conjugate is performed on 3 tumours developing late after radiolabelled antibody injection as well as of the untreated T380 tumour in the nude mice. Blood of 4-5 mice injected with radiolabelled MAb or of untreated mice bearing tumours is obtained weekly after antibody injection and white blood cells are counted. Five mice, finally, having survived for ½ year after preliminary therapy protocols, are examined histologically and by immunoperoxidase staining for remaining viable tumour cells and their CEA expression. Their thyroid, liver, kidney, lung and spleen are analyzed morphologically for radiation damage.

The size of well established tumour grafts increases up to 6 days after radiolabelled antibody injection but then tumour regression for 4-12 weeks sets in.

This must correspond either to a destruction of more than 99% of tumour cells or to the destruction of a lower percentage but accompanied with a marked inhibition of cell proliferation.

A main control group of 13 mice is injected with the same amount of $^{131}$I-labelled intact normal IgG1 and its F(ab')$_2$ fragments. Tumour progression is retarded for 1 to 3 weeks as compared to untreated controls, but no tumour regression is observed.

Results (evolution of tumour size in treated mice and controls) are summarized in the table below. On the day of injection, mean tumour sizes range from 47–50 mm$^3$ in the 4 groups of mice shown in the table. A rapid increase is observed in groups (c) and (d) during the following 28 days. In mice injected with radiolabelled antibodies the mean tumour size after an initial increase up to 122 mm$^3$ decreases to a minimum value of 44 mm$^3$ on day 28 (group a). In group (b) injected with radiolabelled normal IgG, slow but constant tumour progression is observed with a mean tumour size of 449 mm$^3$ on day 28.

Evolution of tumour sizes in treated mice and controls

| Treatment | Number of mice | Mean tumour size in mm$^3$ and standard deviation at the following days after injection | | | | | |
|---|---|---|---|---|---|---|---|
| | | 0 | 6 | 10 | 14 | 21 | 28 |
| (a) $^{131}$I anti-CEA MAb | 13 | 50.2 ± 30 | 122 ± 51 | 105 ± 49 | 76 ± 32 | 57 ± 23 | 44 ± 18 |
| (b) $^{131}$I control IgG | 13 | 47.5 ± 21 | 121 ± 59 | 133 ± 85 | 144 ± 73 | 200 ± 111 | 449 ± 287 |
| (c) anti-CEA MAb | 11 | 49.1 ± 25 | 248 ± 223 | 510 ± 483 | 1034 ± 944 | >1000 | >1000 |
| (d) no treatment | 10 | 47.5 ± 29 | 333 ± 370 | 585 ± 589 | 881 ± 996 | >1000 | >1000 |

New results show that tumour transplanted nude mice can be completely bured from their tumours by using $^{131}$I labelled F(ab')$_2$ fragments of the three MAbs. 8 out of 10 mice survive one year without tumour relapse.

Tumours dissected 24 and 72 h after injection of therapeutic doses of $^{131}$I labelled antibody/fragment mixtures show no histological modification detectable by optical microscopy. In contrast, patchy areas of necrosis and numerous pyknotic cells are observed in the tumours dissected 7 days after injection.

In the animals which survived 6 months after radioimmunotherapy, different organs are analyzed by optical microscopy. Thyroids, kidneys, lungs and spleen look normal.

Absence of mortality among treated mice indicates that the effects of radioimmunotherapy on hematopoiesis are negligible.

EXAMPLE 5

Enzyme-Linked Immunosorbent Assay (ELISA)

5.1 Assay procedure

Polypropylene microtitre plates (Dynatech) are coated over a period of 2 h at 37° C. and overnight at 4° C. with 150 µl of a solution of the monoclonal antibody MAb CE25 (10 µg/ml) in a buffer pH 8.6 (carbonatebuffered 0.9% saline containing 0.02% sodium azide). The plates are washed five times with PBS, and protein-reactive sites still present are saturated by incubation for 1 h at 37° C. with 250 µl of a buffer pH 7.4 (0.2% gelatine and 0.2% NaN$_3$ in PBS). Plates coated in this manner can be kept at 4° C. in this buffer for a few days.

50 µl of a dilution series of a test solution or a standard solution containing purified human CEA, 50 µl of buffer pH 7.4 and 50 µl of a solution of the alkaline phosphatase-labelled monoclonal anti-CEA antibody MAb 35 recognizing a different CEA-epitope diluted 1:100 with buffer pH 7.4 are mixed and incubated in the wells of the microtitre plates for 2 h at 37° C. and for 30 minutes at 4° C. The plates are washed five times with PBS, then incubated for 30 min at 37° C. with 150 µl of a solution of p-nitrophenyl phosphate (1 mg/ml in 10% diethanolamine buffer, 0.5 mM MgCl$_2$, pH 9.8). By measuring the optical density at 405 nm, the amount of released p-nitrophenol is determined, which is proportional to the amount of the bound enzyme phosphatase and hence proportional to the amount of CEA in the test solution.

The ELISA can also be carried out by using enzyme-labelled MAb CE25 and coating the microtitre plates with the monoclonal anti-CEA antibody MAb 35 recognizing a different CEA-epitope.

5.2 Test Kit for ELISA

A test kit for the assay described in Example 5.1 contains:

polypropylene microtitre plates,
20 ml of monoclonal antibody MAb CE25 (10 µg/ml) in carbonate-buffered saline (0.9% NaCl, 0.42% NaHCO$_3$, 0.0072% Na$_2$CO$_3$, 0.02% NaN$_3$),
1 ml of the alkaline phosphatase-coupled monoclonal antibody MAb 35 recognizing a different CEA-epitope (0.3 mg antibody per ml) in Tris buffer (0.05M, 1 mM MgCl$_2$, 1% BSA, 0.02% NaN$_3$, pH 8.0), 2 ml of standard solution containing 5 µg purified human CEA,
300 ml of PBS,
300 ml of buffer pH 7.4 (0.2% gelatine and 0.2% NaN$_3$ in PBS),
50 ml of p-nitrophenyl phosphate (1 mg/ml) in diethanolamine buffer (10%, 0.5 mM MgCl$_2$, 0.02% NaN$_3$, adjusted to pH 8.9 with HCl),
calibration curve,
colour intensity scale,
instruction manual.

EXAMPLE 6

Pharmaceutical Preparation for Parenteral Application 120 mg monoclonal antibody MAb CE25 prepared according to Example 2 are dissolved in 5 ml physiological saline. The solution is passed through a bacteriological filter, and the filtrate filled in an ampoule under aseptic conditions. The ampoule is preferentially stored in the cold, e.g. at −20° C.

We claim:

1. A monoclonal antibody specific for human carcinoembryonic antigen, and derivatives thereof selected from the group consisting of antigen-binding fragments, conjugates with enzymes, fluorescent markers, metal chelates, cytotoxic or cytostatic substances, avidin, biotin, radioactively labelled antibodies and radioactively labelled fragments, characterized in that said antibody and derivatives thereof recognize epitopes of human carcinoembryonic antigen not present on non-specific cross-reacting antigen NCA$_{55}$ or NCA$_{95}$, biliary glycoprotein or granulocytes, and bind to human carcinoembryonic antigen with an affinity of at least $1.3 \times 10^{10}$ to $1.9 \times 10^{10}$ liters/mol and having the designation MAb CE25.

2. A derivative of a monoclonal antibody according to claim 1 which is a conjugate with an enzyme, a fluorescent marker, a metal chelate, a cytostatic or cytotoxic substance, avidin or biotin.

3. A derivative of a monoclonal antibody according to claim 1 which is radioactively labelled.

4. A derivative of a monoclonal antibody according to claim 1 which is a n antigen-binding fragment.

5. A process for the preparation of a monoclonal antibody and derivatives thereof according to claim 1, comprising multiplying hybridoma cells secreting the antibody, either in vitro or in vivo, and, if desired, converting the resulting antibodies into derivatives thereof.

6. A process according to claim 5, comprising injecting antibody secreting hybridoma cells intraperitoneally into Balb/c mice that have optionally been pretreated with a hydrocarbon, and taking, after 8–10 days, ascitic fluid from these animals.

7. A hybridoma cell line which secretes a monoclonal antibody according to claim 1.

8. A process for the preparation of a hybridoma cell line according to claim 7, comprising immunizing Balb/c mice with purified human carcinoembryonic antigen or with an antigenic carrier containing purified human carcinoembryonic antigen, fusing antibody-producing cells of the Balb/c mice with cells of the myeloma P3-NS2/1Ag4, cloning the hybrid cells obtained in the fusion, and selecting cell clones secreting the desired antibodies.

9. A process according to claim 8, comprising immunizing Balb/c mice with saline-extracted purified human carcinoembryonic antigen.

* * * * *